US005270038A

United States Patent [19]
Klimpel et al.

[11] Patent Number: 5,270,038
[45] Date of Patent: Dec. 14, 1993

[54] TUMOR NECROSIS FACTOR RECEPTORS ON MICROORGANISMS

[75] Inventors: Gary R. Klimpel, Santa Fe; David W. Niesel, League City, both of Tex.

[73] Assignee: Board of Regents, The University of Texas System, Austin, Tex.

[21] Appl. No.: 824,112

[22] Filed: Jan. 23, 1992

[51] Int. Cl.[5] .................. A61K 39/02; A61K 39/112; A61K 39/108; A61K 39/00

[52] U.S. Cl. ........................................ 424/88; 424/92; 424/85.1; 435/252.1; 435/252.8; 435/879; 435/849; 435/922; 435/255.4

[58] Field of Search ................ 424/92, 88, 85.1, 85.2, 424/85.4; 435/811, 252.1, 252.8, 255

[56] References Cited

U.S. PATENT DOCUMENTS

| | | | |
|---|---|---|---|
| 4,764,370 | 8/1988 | Fields et al. | 424/93 |
| 4,820,514 | 4/1989 | Cummins | 424/85.4 |
| 5,100,664 | 4/1992 | Doyle et al. | 424/92 |

OTHER PUBLICATIONS

Denis, M. et al., Interleukin-2 and Granulocyte-Marcophage Colony Stimulating Factor Stimulate Growth of a Virulent Strain of *Escherichia coli*, Infection and Immunity, 59(5): 1853–1856, 1991.

Le J. et al., Laboratory Investigation 56(3): 234–248, 1987.

Porat, R. et al., Enhancement of Growth of Virulent Strains of *Escherichia coli* by Interleukin-1, Science 254: 430–432, 1991.

Henney, C. S., Potential Therapeutical Applications of Interleukin-1, from a published transcript of the proceedings from the "International Conference on the Clinical Impact of Interleukins" at the Royal College of Physicians in London (Apr. 1989).

*Primary Examiner*—Christine M. Nucker
*Assistant Examiner*—Julie Krsek-Staples
*Attorney, Agent, or Firm*—Arnold, White & Durkee

[57] ABSTRACT

Cytokine receptors for tumor necrosis factor α which are found on microorganisms may, if bound with exogenous TNFα, enhance the response of natural killer cells activated by the microorganisms, or increase TNFα production by peripheral blood lymphocytes treated with the microorganisms. Microorganisms with receptor-bound exogenous TNFα have enhanced cellular invasion ability which may change the immune response thereto. Clinical and pharmaceutical applications of these discoveries including vaccines with increased efficacy are provided.

12 Claims, 3 Drawing Sheets

TUMOR NECROSIS FACTOR RECEPTORS ON MICROORGANISMS

The United States Government has rights in the present patent application because certain related research was supported by National Institutes of Health Grant No. A-123731.

BACKGROUND OF THE INVENTION

The invention relates generally to the discovery of cytokine receptors on microorganisms, and more specifically to new methods and products in medical treatment and research related to the discovery. Cytokines produced by monocytes/macrophages are called monokines, and those produced by lymphocytes are called lymphokines. Stimuli for their production include endotoxin and Gram-negative bacteria. One cytokine of particular interest is tumor necrosis factor $\alpha$ (TNF$\alpha$).

TNF$\alpha$ is an inflammatory cytokine which has numerous biological activities and is believed to play important roles, not only in host defense but also in some of the pathological sequelae associated with bacterial infections. Receptor(s) for TNF$\alpha$ are found on most somatic cells, and they have recently been characterized and cloned. Biological effects of TNF$\alpha$ and other cytokines binding to eukaryotic cells are well known.

For example, it is now well established that cytokines play important roles in regulating aspects of the immune response. Cytokines have been shown to be essential for host defense against viruses, tumors and bacterial infections. There is, however, a delicate balance between when a cytokine is advantageous to a host and when it contributes to the pathology of a disease. Thus, knowledge of how to make the choice between administering a cytokine and blocking its action in a disease process could be a valuable tool in clinical medicine. The need for such knowledge is rapidly increasing as cytokines and cytokine blockers become more readily available.

Many cytokines have now been cloned and new cytokines are constantly being discovered and cloned. Recombinant cytokines are now also being used in clinical trials all over the world. Recently, much attention has been focused on identifying and cloning cytokine receptors on eukaryotic cells previously identified as being targets for the many cytokines produced by the immune system. But similar work on pathogenic cells such as bacteria has not been published; there are no reports of TNF$\alpha$ or any other cytokine binding to bacteria until quite recently (1A).

SUMMARY OF THE INVENTION

The present invention concerns findings that microorganisms, including bacteria and imperfect fungi, have cytokine receptors. A microorganism receptor for TNF$\alpha$ is of particular interest. With receptor-bound TNF$\alpha$ microorganisms more effectively enhance natural killer (NK) cell activity and induce the production of TNF$\alpha$ by human peripheral blood lymphocytes (PBL's). Further, bacteria with receptor-bound TNF$\alpha$ are taken up by macrophages and epithelial cells to a much greater extent than bacteria without receptor-bound TNF$\alpha$. Although it is known that many cytokines are produced as a consequence of bacterial interaction with monocytes/macrophages or lymphocytes, there are few reports of bacteria and none of imperfect fungi having receptors for cytokines. None previously have reported microorganisms becoming more immunogenic as a result of bound cytokine effects. In this regard, it was found that coating *S. typhimurium* with TNF$\alpha$ resulted in a complex which induced higher levels of antibody in vivo to this bacterium as compared to animals given uncoated bacteria.

One form of the invention is a composition comprising microorganisms having receptors for TNF$\alpha$ or other cytokines, with exogenous cytokines such as TNF$\alpha$ bound thereto. These are novel compositions of matter which those skilled in the art will recognize as having many uses. Specific applications include those where the source of exogenous cytokines such as TNF$\alpha$ is living eukaryotic cells, as well as those where the source is a recombinant microorganism or process based thereon.

Among the microorganisms to which the invention may be applied are Gram-positive or Gram-negative bacteria, as well as imperfect fungi. Specific examples of microorganisms to which the invention may be applied include *Candida albicans*, *Salmonella typhimurium*, *Shieglla flexneri*, and *Escherichia coli*. Those skilled in the art will recognize that any microorganism with receptors for cytokines, including TNF$\alpha$, can be used in applications of the invention.

The compositions or methods of the invention may be used for activating human NK cells by treating them with microorganisms having receptors for TNF$\alpha$ or other cytokines to which exogenous TNF$\alpha$ or other cytokines have been bound. Analogously, human PBL's may be treated with microorganisms having receptor-bound exogenous TNF$\alpha$ or other cytokines to stimulate the production of additional cytokines such as TNF$\alpha$ by the PBL's. Other cells may be substituted for the human NK and PBL cells in these applications.

The cellular invasion ability of microorganisms may be enhanced by application of the invention by binding exogenous TNF$\alpha$ or other cytokines to microorganism receptors. Because alteration of the cellular invasion ability of a microorganism changes the cellular response to such microorganisms, the immune response will also change. Those skilled in the art will appreciate that vaccines comprised of components with enhanced invasion ability may have improved efficacy.

Applications of the invention include the use of bacterial-derived receptors for TNF$\alpha$ or other cytokines for isolating and purifying particular cytokines. Additionally, a more effective clinical treatment of diseases involving the modulation of the immune system by inhibiting or enhancing the effects of TNF$\alpha$ or other cytokines is feasible. Pharmaceutical applications of the invention may include the use of bacteria with receptor-bound TNF$\alpha$ or another cytokine to make the bacteria better antigens and thereby improve the efficacy of vaccines by enhancing host immune response. The latter application may include preparation of vaccines for human and animal use. Those skilled in the art will recognize that other cytokines may substitute for TNF$\alpha$, depending on the application.

DESCRIPTION OF THE PREFERRED EMBODIMENTS

Figure 1:
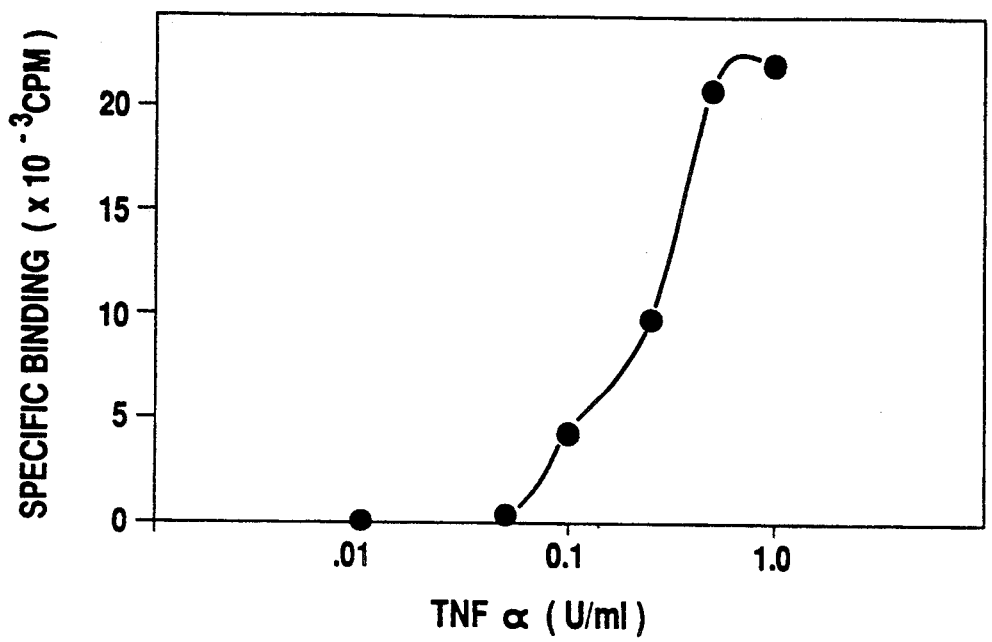
FIG. 1. Saturation binding curve of $^{125}$I-TNF$\alpha$ after 40 min at 37° C. with *Shigella flexneri*.

The present invention relies in part on the fact that receptors for cytokines such as TNFα are found on microorganisms such as Gram-negative bacteria, Gram-positive bacteria, and the yeast form of *Candida albicans*. Other aspects of the invention derive from the fact that bacteria with receptor-bound TNFα enhance NK cell activity (Table 1) and induce TNFα production from human PBL's (Table 2) to a much greater extent than bacteria without receptor-bound TNFα. Such bacteria are also taken up by macrophages and epithelial cells more avidly than bacteria without TNFα on their surface, viz., a virulence property is altered by the presence of TNFα. Coating bacteria with TNFα resulted in a more immunogenic antigen which resulted in higher levels of antibody being produced in mice (Table 4). These observed TNFα-related effects support the claimed clinical and laboratory applications in the present invention. Those skilled in the art will recognize that both other cytokines and other microorganisms than those exemplified herein may be quite analogously utilized.

TABLE 1

NK cell activation by TNFα coated bacteria

| Culture conditions | NK cell activity %$^{51}$Cr release E:T ratio | | |
|---|---|---|---|
| | 3:1 | 12:1 | 50:1 |
| Human PBL plus: | | | |
| Medium | 3 | 10 | 32 |
| IL2 | 15 | 40 | 60 |
| *S. flexneri* | 6 | 14 | 38 |
| *S. flexneri* coated with TNFα | 10 | 25 | 49 |
| *S. typhimurium* | 8 | 12 | 30 |
| *S. typhimurium* coated with TNFα | 13 | 29 | 52 |

Human PBL are incubated 18 hr with one of the following: 1) IL2 500 u/ml, 2) 10$^5$ CFU of *S. flexneri* either untreated or coated with TNFα, or 3) 10$^5$ CFU of *S. typhimurium* either untreated or coated with TNFα. NK cell activity is assessed using a 4 hr $^{51}$Cr release assay with K562 tumor cells.

TABLE 2

TNF production by human PBL stimulated with TNFα-coated *S. flexneri*

| Culture conditions | TNF u/ml |
|---|---|
| Human PBL plus: | |
| Medium | 12 |
| *S. flexneri* | 13 |
| *S. flexneri* coated with TNFα | 109 |

Human PBL are incubated 18 hr with 1) medium, 2) *S. flexneri*, or 3) *S. flexneri* coated with TNFα. Supernatants from these cultures are assessed for TNF bioactivity using the L929 assay.

The following examples are presented to describe preferred embodiments and utilities of the present invention and are not meant to limit the present invention unless otherwise specified in the claims appended hereto. Taken together, the examples illustrate the best mode of implementing the invention as it is currently understood.

EXAMPLE 1

TNFα Binding to *Shigella Flexneri*

TNFα binding to a *Shigella Flexneri* is investigated using $^{125}$I-labeled human recombinant TNFα and bacterium-$^{125}$I-TNFα complexes quantitated by filtration. $^{125}$I-labeled recombinant human TNFα (200–800 Ci/mMol) is obtainable from Amersham Corp., Arlington Heights, Ill., or may be produced using the iodogen method with rhTNFα obtained from UBI Inc., Lake Placid, N.Y. Unlabeled recombinant human TNFα ($2 \times 10^7$ units/mg) and TNFβ ($3 \times 10^7$ units/mg) are available from Genzyme, Boston, Mass. Bacteria from overnight cultures of *S. flexneri* serotype 2a, strain SA100 are grown to mid-logarithmic phase, then incubated 10 min at 37° C. with 0.01% azide in RPMI medium. Four *Shigella flexneri* strains of this serotype are available from the American Type Culture Collection, 12301 Parklawn Drive, Rockville, Md. 20852-1776. Treated-bacteria ($2 \times 10^9$ cfu) are then washed and incubated in 250 μl of PBS containing 1% heat inactivated FCS or 1% BSA plus varying concentrations of labeled or unlabeled TNFα or TNFβ. After appropriate incubation at 37° C. with mixing every 10 min, bacteria-TNF mixtures are transferred to a syringe (10 ml) equipped with a 0.45 μm nitrocellulose filter. Tubes (BSA-coated microfuge) which contained bacteria-TNF mixtures are washed with 250 μl of RPMI, and this volume added to the syringe-filter. Bacteria are then isolated by filtration and filters containing bacteria washed with 1 ml of RPMI. Filters are then assessed for the amount of bound $^{125}$I-TNFα. Filters used in these experiments are pretreated with FCS. $^{125}$I-TNFα binding to filters in the absence of bacteria is ≤6% of the total cpm added to the binding mixture. This value is always subtracted from cpm obtained from $^{125}$I-TNF-bacteria complexes isolated by filtration. Non-specific binding to bacteria is assessed using ≧100-fold excess of unlabeled TNFα. Non-specific binding is usually about 10% of total bound cpm. Scatchard analysis is performed as described by Stuart.

$^{125}$I-TNFα binding to *S. flexneri* varies among different commercial lots of $^{125}$I-TNFα. This appears to correlate with the level of biological activity retained by the $^{125}$I-labeled TNFα. Little binding is detected when $^{125}$I-TNFα has <20% of its biological activity as measured by the L-929 bioassay. In this regard, over one-half of the commercially obtained lots of $^{125}$I-TNFα have lost 80–90% of their biological activity and give low levels of binding to *S. flexneri*.

$^{125}$I-TNFα binding to azide-treated versus untreated bacteria is identical during the first 20 min of incubation. However, untreated bacteria have a doubling time of around 30–40 min and consistently bind more TNFα than azide-treated bacteria at time periods longer than 20 min. Data presented above and in Table 1 are obtained using azide-treated bacteria when binding is assessed at 37° C. Non-azide-treated bacteria are used when binding is assessed at 4° C., which is optimal at 4 hr incubation. Scatchard analysis of data obtained from binding experiments done at 4° C. gives a Kd of 3.0 nM with 215 binding sites for TNFα per bacterium.

Figure 2:
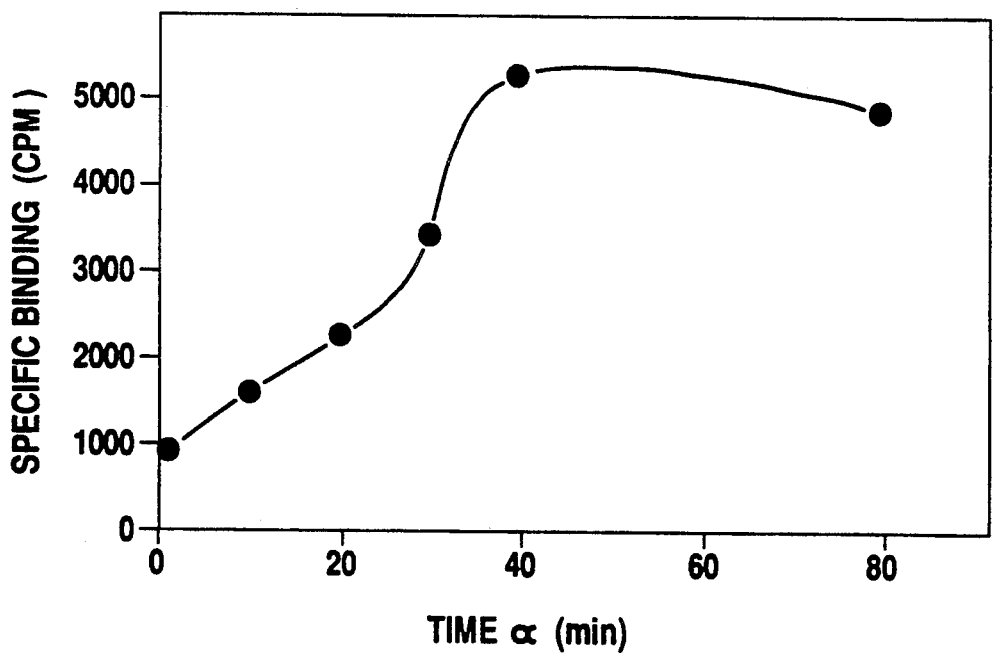
FIG. 2. Time course of $^{125}$I-TNF$\alpha$ binding by *Shigella flexneri* at 37° C. showing binding is saturable, with optimal binding occurring at 40 minutes at 37° C.
Figure 3:
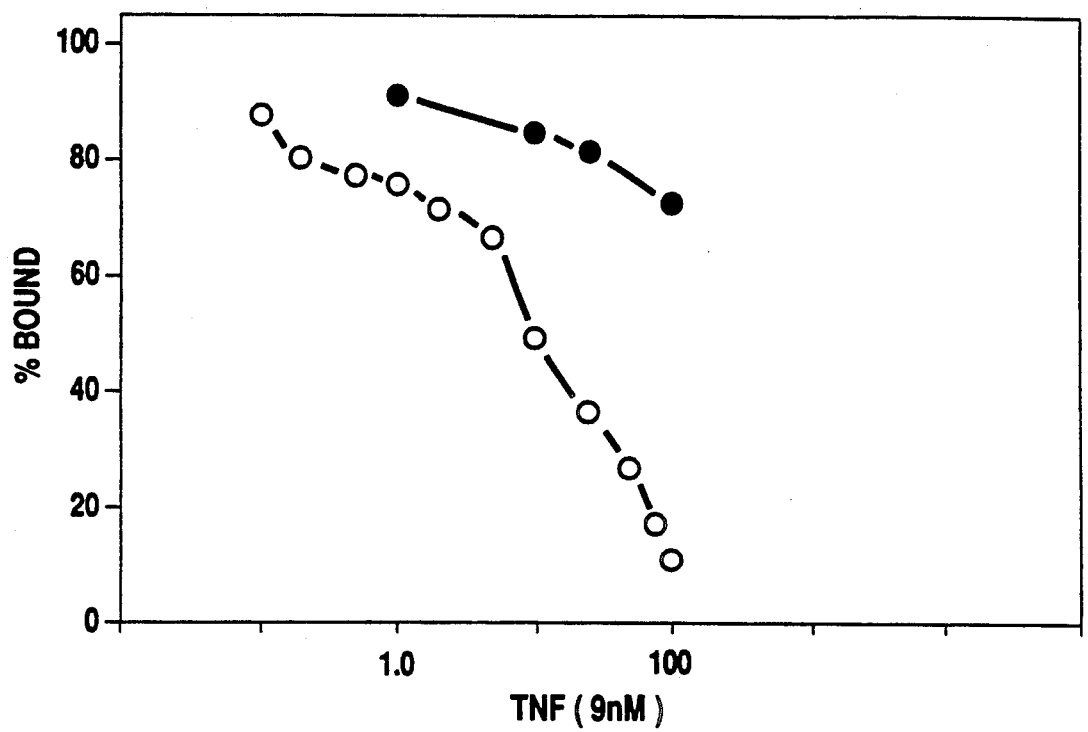
FIG. 3. Competition of TNF$\alpha$ (open circles) and TNF$\beta$ (solid circles) with $^{125}$I-TNF$\alpha$ for binding to *Shigella flexneri*. Unlabeled TNF$\beta$ is ineffective at competing with $^{125}$I-TNFα.
Figure 3A:
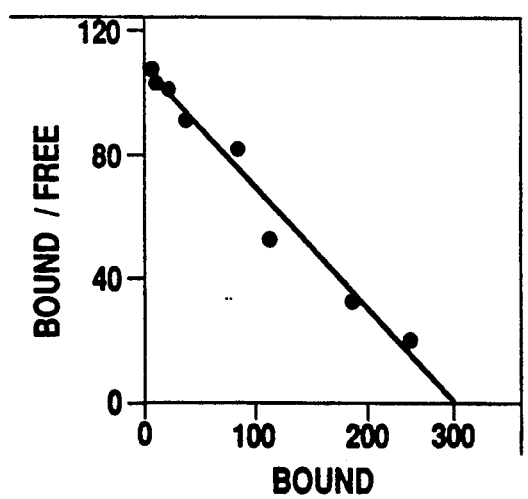
FIG. 3A shows Scatchard analysis indicating a Kd of 2.5 nM, with 276 binding sites for TNFα per bacterium.

As illustrated in FIGS. 1-3, S. flexneri binds significant levels of $^{125}$I-TNFα. This binding is saturable with optimal binding occurring at 40 min when binding is performed at 37° C. (FIGS. 1 & 2). FIG. 2 shows the time course of $^{125}$I-TNFα binding using 0.1 nM $^{125}$I-TNFα ($3-4 \times 10^4$ cpm). When binding is measured at 4° C., optimal binding occurs at 4 hr. FIG. 3 shows the competition of TNFα (open circles) and TNFβ (solid circles) with $^{125}$I-TNFα for binding to S. flexneri. FIG. 3A shows Scatchard analysis indicating a Kd of 2.5 nM, with 276 binding sites for TNFα per bacterium. The binding of $^{125}$I-TNFα to S. flexneri is inhibited by various concentrations of unlabeled TNFα, but unlabeled TNFβ is ineffective at competing with $^{125}$I-TNFα. In contrast, TNFα receptors on eukaryotic cells can be occupied by both TNFα and TNFβ. Thus, the bacterial receptors for TNFα appear to differ from TNFα receptors on eukaryotic cells with regard to binding specificity for TNFα versus TNFβ.

EXAMPLE 2

TNFα Binding to Bacteria

The ability to bind TNFα is not exclusive to Shigella flexneri. An avirulent Escherichia coli and a virulent Salmonella typhimurium both bind significant levels of $^{125}$I-TNFα (Table 3). Further, both a virulent (SA100) and an isogeneic non-pathogenic S. flexneri strain (SA100NI) appear to bind comparable levels of $^{125}$I-TNFα (Table 3). These data indicate that bacteria-TNFα binding may be common property of both virulent and avirulent gram-negative bacteria.

No difference is found between the levels of TNFα bound by rough versus smooth strains of Salmonella. However, heating, (52° C./3 min), formalin fixation or trypsin treatment of bacteria results in complete to partial reduction of TNFα binding (Table 3), indicating that bacteria-encoded protein forms at least a part of the TNFα receptor.

TABLE 3

TNFα binding to bacteria

| | Bacterium | TNFα Specific binding (cpm) at: | |
|---|---|---|---|
| | | 4° C. | 37° C. |
| Exp. 1 | S. flexneri (SA100NI) | 6591 ± 124 | 5994 ± 404 |
| | E. coli | 5801 ± 58 | 6150 ± 150 |
| | S. typhimurium | 4951 ± 160 | 5850 ± 300 |
| Exp. 2 | S. flexneri (SA100) | | |
| | untreated | 7065 ± 48 | 5226 ± 73 |
| | formalin-fixed | 5818 ± 33 | 4176 ± 66 |
| | heat-treated | 3199 ± 91 | 3056 ± 8 |
| Exp. 3 | S. flexneri (SA100) | | |
| | untreated | 3588 ± 99 | |
| | trypsin-treated | 327 ± 97 | |
| Exp. 4 | C. albicans | 6053 ± 120 | 5410 ± 91 |

$^{125}$I-TNFα binding to different bacteria was assessed. Bacteria ($2 \times 10^9$) are incubated with 0.1 nM $^{125}$I-TNFα ($3-4 \times 10^4$ cpm) for 40 min at 37° C. or for 4 hr at 4° C. A laboratory strain of E. coli (DH5α) and a rough strain of S. typhimurium (TML) are grown and treated as described in FIG. 1 for S. flexneri. Candida albicans were grown to mid-logarithmic phase and washed twice. $^{125}$I-INFα binding to Candida albicans was assessed using $5 \times 10^7$ organisms and using assay conditions exactly as described for $^{125}$I-TNFα binding to bacteria. S. flexneri are also assessed for TNFα binding following heat treatment (52° C. for 3 min), fixation by 1% formaldehyde, or by trypsin treatment. Trypsin treatment of bacteria is achieved by incubating $4 \times 10^9$ S. flexneri (SA100) in 10 ml of PBS with trypsin (100 μg/ml, Sigma, St. Louis, MO) for 30 min at 37° C. Soybean trypsin inhibitor (100 μg/ml, Sigma) is then added and after 15 min at 37° C. the bacteria are pelleted and washed. Trypsin treated or control treated bacteria are then assessed for their ability to bind $^{125}$I-TNFα as described in FIG. 1. Data presented are the mean (SD) of duplicated determinations.

EXAMPLE 3

Biological Consequences of TNFα Binding to Shigella Flexneri

Important virulence factors of S. flexneri are its ability to penetrate and replicate within epithelial cells of the intestinal mucosa, resulting in subsequent tissue damage. These factors are investigated in HeLa cells by pretreatment of S. flexneri SA100 with TNFα. S. flexneri (SA100 or SA100NI) are incubated in 1 ml of RPMI-1640 with or without varying concentrations of TNFα. After 4 hr at 4° C., bacteria ($10^3$ cfu/ml) are pelleted by centrifugation (1500 xg) and washed once with 4 ml of RPMI. Bacteria (pretreated with media vs TNFα) are then assessed for their ability to invade HeLa cells. HeLa cell invasion is assessed by using an agarose-agar overlaying procedure as previously described.

Figure 4:
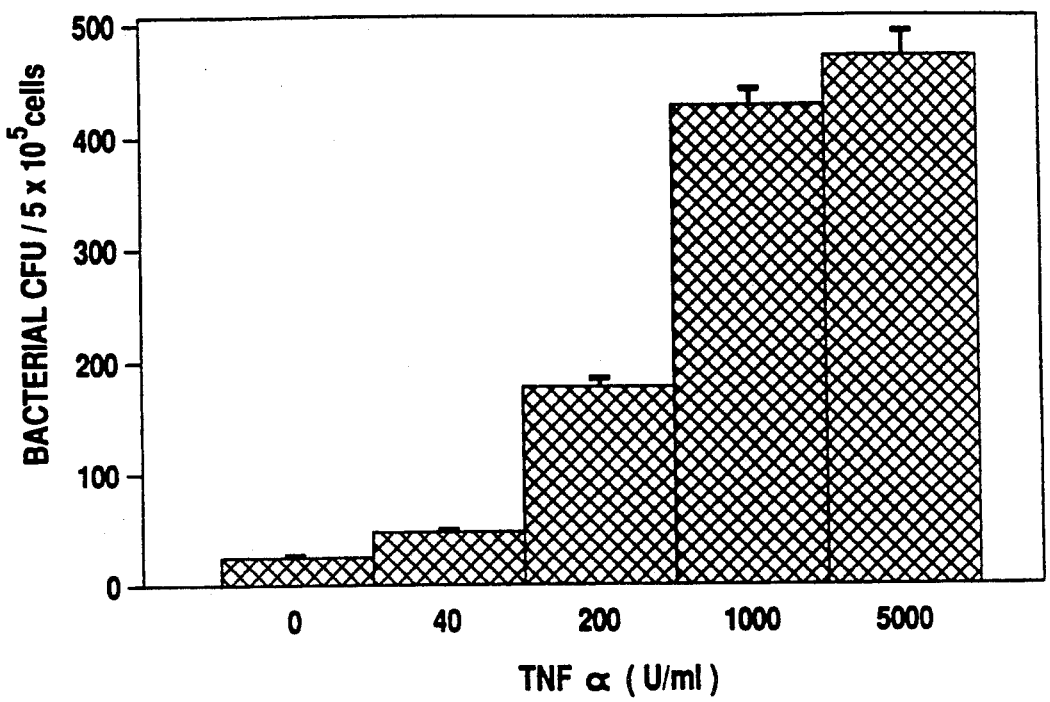
FIG. 4. HeLa cell invasion by (virulent) *S. flexneri* (SA100) is increased up to 20-fold in bacteria pretreated with TNFα, compared with invasion by untreated bacteria.

Data presented are from triplicate determinations and from one representative experiment of 10 experiments. The results show a dramatic enhancement of HeLa cell invasion (FIG. 4). S. flexneri SA100 ($10^3$ cfu) pretreated with 5000 U of TNFα for 4 hr at 4° C. and then washed twice has a 20-fold enhancement in cellular invasion.

Figure 5:
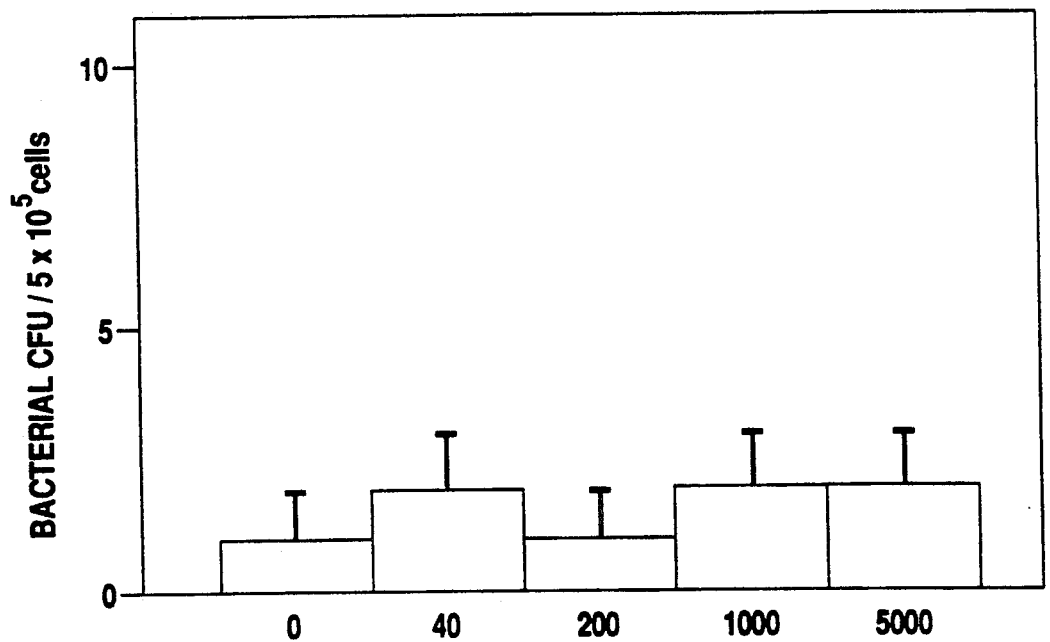
FIG. 5. HeLa cell invasion by (avirulent) *S. flexneri* (SA100NI) is essentially unchanged in bacteria pretreated with TNFα, compared with invasion by untreated bacteria.

It is apparent that enhancement of cellular invasion is dependent upon bacterial virulence factor(s) because non-invasive S. flexneri can not be converted to an invasive form by TNFα binding. A non-invasive isogeneic variant of S. flexneri, SA100NI, which binds equivalent levels of $^{125}$I-TNFα (Table 3) does not invade HeLa cells after TNFα pretreatment (FIG. 5). The mechanism(s) involved in the enhanced cellular invasion by TNFα-Shigella complexes is unknown, but could possibly result from enhanced interaction with the cell surface.

EXAMPLE 4

Enhanced Immunogenic Potential of TNFα-Coated S. Typhimurium

Coating a pathogen with a cytokine was found to result in a more immunogenic antigen. Salmonella typhimurium ($10^8$) were incubated with rTNFα (10,000 U) in a volume of 250 ml. After 4 hours at 4° C. the bacteria-TNFα complexes were formalin-fixed, washed twice and injected (ip) into C57B1/6 mice. As a control, Salmonella were treated in an identical fashion in medium with no TNF. Mice were bled at 6 days post challenge. Results of a representative experiment are illustrated in Table 4.

TABLE 4

Enhanced Antibody Production
in vivo by TNF-Coated S. Typhimurium

| Mice Immunized With | Antibody to TML ELISA Assay (OD Units) |
|---|---|
| S. typhimurium (TML) | .6523 × .15 |
| S. typhimurium (TML) coated with TNFα | 1.075 × .31 |

C57B1/6 mice (5) were challenged (ip) with $10^8$ formalin-fixed TML which had been pretreated with $10^4$ of rTNFα. Serum from individual mice were obtained at 6 days and assessed for antibody to TML by ELISA assay. Data is mean ± SD OD units from 5 mice per group.

Coating Salmonella with TNFα resulted in an enhanced antibody response to Salmonella. These data indicate that coating a pathogen with TNFα can enhance the immune response to that pathogen. These results could be applied for the preparation of vaccines for both human and animal use. Improved vaccines could result from coating any pathogen with cytokines such as interleukin-1 (IL1), interleukin-2 (IL2) or interferon (IFN). The coating could be easily performed as described above or by cross-linking the cytokine onto the pathogen. Additionally, deactivated microorganisms or antigenic microorganism surface components retaining bound cytokines could be used as administered material in the usual course of human or domestic animal vaccination. Oral administration of cytokine-containing avirulent microorganism strains is a preferred mode of immunization, of course when the elicited immunity precludes adverse effects of analogous virulent microorganisms.

REFERENCES

The following references are incorporated in pertinent part in the specification for the reasons therein.

1.A Porat et al., Science 254, 430 (1991).
1. Beutler, B. and Cerami, A. Ann. Rev. Immunol. 7, 625-655 (1989).
2. Sherry, B. and Cerami, A. J. Cell Biol. 107, 1269-1277 (1988).
3. Le, J. and Vilcek, J. Lab. Invest. 56, 234-248 (1987).
4. Nakane, A., Minagawa, T., and Kato, K. Infect. Immun. 56, 2563-2569 (1988).
5. Kindler, V., Sappino, A. P., Grau, G., Piquet, P. F., and Vassalli, p. Cell 56, 731-740 (1989).
6. Tracey, K. J., Fong, Y., Hesse, D. G., Manogue, K. R., Lee, A. T., Kuo, G. L., Lowry, S. F., and Cerami, A. Nature 330, 662-664 (1978).
7. Klimpel, G. R., Shaban, R., and Niesel, D. W. J. Immunol. 145, 711-717 (1990).
8. Grau, G., Fajardo, L. F., Piquet, P. F., Allet, B., Lambert, P. H., and Vassalli, P. Science 237, 1210-1212 (1987).
9. Aggarwal, B. B., Essalu, T. E., and Hass, P. E. Nature 565-567 (1985).
10. Smith, C. A., Davis, T., Anderson, D., Solam, L., Beckmann, M. P., Jeryz, R., Dower, S. K., Cosman, D., and Goodwin, R. G. Science 248, 1019-1023 (1990).
11. Schall, T. J., Lewis, M., Koller, K. J., Lee, A., Rice, G. C., Wong, G. H. W., Gatanaga, T., Granger, G. A., Lentz, R., Raab, H., Kohr, W. J., and Goeddel, D. V. Cell 61, 361-370 (1990).
12. Owen-Schaub, L. B., Crump, W. L. III, Morin, G. I., and Grimm, E. A. J. Immunol. 143, 2236-2241 (1989).
13. Hess, C. B., Niesel, D. W., Homgren, J., Jonson, G., and Klimpel, G. R. Infect. Immun. 58, 399-405 (1990).
14. Sansonnetti, P. J., Kopecko, D. J., and Formal, S. B. Infect. Immun. 35, 852-860 (1982).
15. Baird, A., Florkiewicz, R. Z., Maher, P. A., Kaner, R. J., and Hajjar, D. P. Nature 348, 344-346 (1990).
16. Ullberg, M., Kronvall, G., Karlsson, I., and Wiman, B. Infect. Immun. 58, 21-25 (19990).
17. Padda, J. S. and Schryvers, A. B. Infect. Immun. 58, 2972-2976 (1990).
18. Kronvall, G., Quie, P. G., and Williams, R. D., Jr. J. Immunol. 104, 273-278 (1970).
19. Visai, L., Speziale, P., and Bozzini, S. Infect. Immun. 58, 449-455 (1990).
20. Fröman, G., Switalski, L. M., Faris, A., Wadström, T., and Höök, M. J. Biol. Chem. 259, 14899-14905 (1984).
21. Lopes, J. D., dos Reis, M., and Brentani, R. R. Science 229, 275-277 (1985).
22. Holderbaum, D., Hall, G. S., and Ehrhart, L. A. Infect. Immun. 54, 359-364 (1986).
23. Niesel, D. W., Hess, C. B., Cho, Y. J., Klimpel, K. D., and Klimpel, G. R. Infect. Immun. 52, 828-833 (1986).
24. Stuart, C. A. Comp. Biochem. Physiol. 84B, 167-172 (1986).

Changes may be made in the construction, operation and arrangement of the various microorganisms, cytokines, steps and procedures described herein without departing from the concept and scope of the invention as defined in the following claims.

What is claimed is:

1. A composition consisting essentially of a Gram-negative bacterial or imperfect fungal microorganism having exogenous TNFα bound to a microorganism TNFα receptor.

2. The composition of claim 1 wherein the microorganism is a Gram-negative bacteria.

3. The composition of claim 1 wherein the microorganism is *Salmonella typhimurium, Shigella flexneri*, or *Escherichia coli*.

4. The composition of claim 1 wherein the microorganism is *Candida albicans*.

5. The composition of claim 1 wherein the microorganism is an imperfect fungi.

6. The composition of claim 5 wherein the imperfect fungi is *Candida albicans*.

7. A method of producing a vaccine of improved efficacy, the method comprising the steps of:
   identifying Gram-negative bacteria or imperfect fungi against which immunity is desired and which have TNFα receptors;
   binding receptors of said bacteria or imperfect fungi with exogenous TNFα; and
   preparing a pharmaceutically acceptable composition usable as a vaccine and consisting essentially of said Gram-negative bacteria or imperfect fungi having exogenous TNFα bound to said receptors, said bacteria or fungi being deactivated or fragmented to antigenic surface components and retaining bound TNFα.

8. The method of claim 7 wherein imperfect fungi are used.

9. The method of claim 7 wherein Gram-negative bacteria are used.

10. The method of claim 7 wherein the bacteria are *Salmonella typhimurium, Shigella flexneri*, or *Escherichia coli*.

11. A vaccine for induction of immunity to a Gram-negative bacterial or imperfect fungal microorganism consisting essentially of a preparation with tumor necrosis factor α bound to an inactivated microorganism or a surface component thereof.

12. A composition for the induction of immunity to a Gram-negative or imperfect fungal pathogen consisting essentially of a preparation with TNFα bound to an inactivated pathogen or pathogen component.

* * * * *